US00PP12851P2

(12) United States Plant Patent
Evers

(10) Patent No.: US PP12,851 P2
(45) Date of Patent: Aug. 13, 2002

(54) ROSE PLANT NAMED 'TANROSTAX'

(75) Inventor: Hans-Jürgen Evers, Uetersen (DE)

(73) Assignees: Rosen Tantau Mathias; Tantau Nachfolger, both of (DE)

( * ) Notice: Subject to any disclaimer, the term of this patent is extended or adjusted under 35 U.S.C. 154(b) by 0 days.

(21) Appl. No.: 09/438,730

(22) Filed: Nov. 11, 1999

(51) Int. Cl.[7] ..... A01H 5/00

(52) U.S. Cl. ..... Plt./102

(58) Field of Search ..... Plt./102, 103, 104

(56) References Cited

PUBLICATIONS

The New Royal Horticultural Society Dictionary of Gardening, 1992, The MacMillan Press Limited, vol. 4, R to Z, p. xivi.*

* cited by examiner

*Primary Examiner*—Bruce R. Campell
*Assistant Examiner*—June Hwu
(74) *Attorney, Agent, or Firm*—Webb Ziesenheim Logsdon Orkin & Hanson, P.C.

(57) ABSTRACT

The new cultivar is a variety of dwarf rose plant having a broad bushy growth habit. The light pink flowers are small and high-centered. The plant exhibits good winter hardiness, resistance to most diseases, repeated blooming and is easily propagated on its own roots.

1 Drawing Sheet

BACKGROUND OF THE NEW PLANT

The present invention includes a new and distinct cultivar of *Rosa lucinda* known by the varietal name 'Tanrostax'.

The new plant is a spontaneous mutation (sport) of the unpatented variety 'Tanotax' (German Registration No. ROS 836). The plant was discovered by the breeder on the Tanotax plantation in Ueterson, Germany. The plant can be propagated asexually on *Rosa canina* rootstock or on its own roots.

The variety is distinguishable by its very good winter hardiness, repeated blooming, disease resistance and easy propagation on its own roots. The new variety has brighter petal color than 'Tanrostax'. Continued observations from the vegetative cuttings in Uetersen, Germany have confirmed that the distinguishing features of this new cultivar come true, remain stable and are retained through successive propagations.

DESCRIPTION OF THE DRAWING

The accompanying photographic drawing illustrates the new cultivar. Colors are described in reference to The Royal Horticultural Society (London) Colour Chart.

DESCRIPTION OF THE NEW PLANT

The following description sets forth the characteristics of the new cultivar at two years of outdoor growth in Northern Germany.

The plant:
- *Botanical name.*—*Rosa lucinda.*
- *Growth habit.*—Low and spreading.

Size:
- *Height.*—60–80 cm.
- *Width.*—60–70 cm.

Habit: Low and spreading shrub.
Growth vigor: Strong.
Wood color:
- *Immature.*—Green Group 138A.
- *Mature.*—Greyed-Orange Group 165B.

Thorns:
- *Color.*—Immature: Greyed-Purple Group 187D. Mature: Greyed-Purple Group 187A.
- *Size.*—0.4 cm long.
- *Shape.*—Hooked downard.
- *Location on stem and branches.*—Around the stem and with a few small prickles under the leaves.

Disease resistance: Resistant to black spot.
Hardiness: Very good in Northern Germany where mid-January temperature can be −12° C.

FOLIAGE

Arrangement: Alternate.
Number of leaflets on typical stem leaves: 5–7.
Leaflets:
- *Size.*—2.5 cm wide; 6 cm long.
- *Color.*—Medium Green. Upper surface: Green Group 139C. Lower surface: Green Group 138C.
- *Shape.*—Apex: Pointed. Base: Truncated.
- *Texture.*—Leathery.
- *Margin.*—Serrate.

Petiole rachis:
- *Color.*—Yellow-Green Group 146 with intonation of Red Group 142C.
- *Texture.*—Smooth; no prickles.
- *Stipules.*—Size: 0.6 cm wide; 3 cm long. Texture: Smooth. Shape: Pectinate. Color: Upper surface: Yellow-Green Group 146A. Lower surface: Yellow-Green Group 146C.

BUD

Size: 0.8 cm wide; 1.2 cm long.
Shape: Pointed ovoid.
Color: Red Group 36A.
Color changes during opening: Orange-Red Group 35D.
Sepals:
- *Color.*—Green Group 138B.
- *Texture.*—Covered in fine hairs.

*Apex.*—Pointed.
*Size.*—0.2 cm wide; 1.2 cm long.
Receptacle:
*Color.*—Green Group 137C.
*Shape.*—Funnel.
*Texture.*—Smooth.
*Size.*—0.5 cm in diameter.
Peduncle:
*Color.*—Green Group 138B, in sunlight more to Red Group 41D.
*Length.*—2.4 cm.
*Strength.*—Stiff.
*Texture.*—Glandular.
Foliar appendages on peduncle:
*Length.*—3.4 cm long.
*Width.*—0.5 cm wide.
*Color.*—Green Group 141A in middle and Yellow-Green Group 146A towards edge.

FLOWER

Borne (number in clusters): 7–15.
Size (diameter): 5 cm.
Form: High-centered.
Petals:
*Number per flower.*—25–28.
*Color.*—Upper surface: Red Group 49A when half open to fully open. Lower surface: Red Group 49B when half open to fully open. Basal spot: Red Group 39D. Color changes with maturity: Petals brighten at the third day; in strong sunlight become Orange-White Group 159A.
*Texture.*—Soft.
*Size.*—2 cm wide; 2.2 cm long.
*Shape.*—Overall: Lanceolate. Apex: Rounded. Base: Pointed.
*Margin.*—Entire, slightly reflexed on fully opened, outermost petals.
*Persistence.*—Petals drop off cleanly before drying.
*Lastingness.*—Approximately 5–7 days as cut flowers; about 14 days as garden plant.
*Petaloids.*—Elongated; 0.2 cm long; smooth; colored as petals.
Fragrance: None.
Blooming period: In Germany, mid-June to mid-November.

REPRODUCTIVE ORGANS

Stamens:
*Number.*—About 25.
*Anther.*—Length: 0.1 cm long. Color: Orange Group 26A.
*Filament.*—Length: 0.3 cm long. Color: Yellow-Orange. Pollen color: Orange.
Pistils:
*Number.*—10–15.
*Style.*—Color: Green Group 136D. Length: 2 cm long.
*Stigma.*—Color: Green Group 135D. Length: 2 cm long.
Hip/seed: None produced.

I claim:

1. A new and distinct variety of rose plant substantially as shown and described.

* * * * *

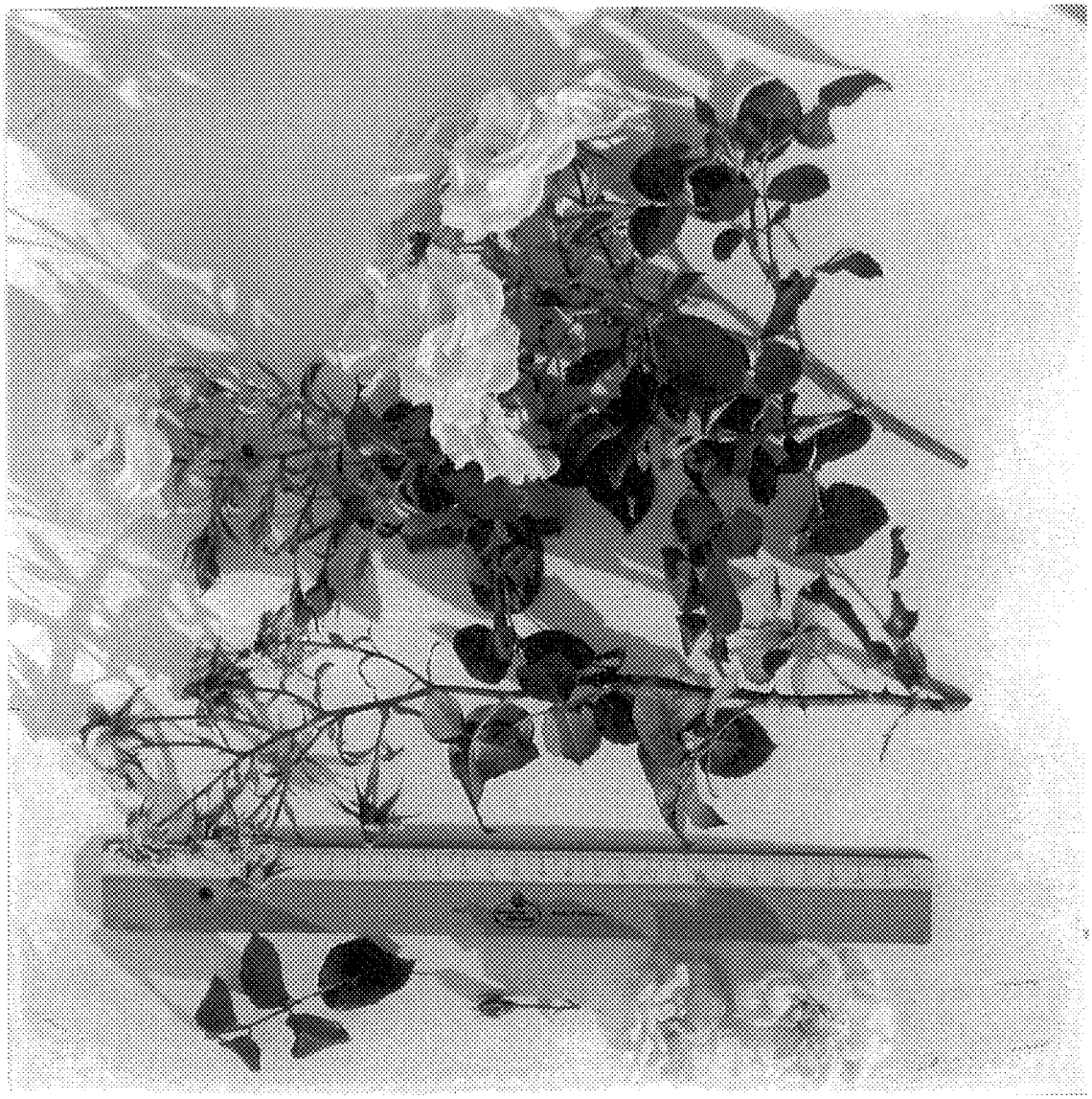

UNITED STATES PATENT AND TRADEMARK OFFICE

CERTIFICATE OF CORRECTION

PATENT NO. : PP 12,851 P2
DATED : August 13, 2002
INVENTOR(S) : Hans-Jurgen Evers It is certified that error appears in the above-identified patent and that said Letters Patent is hereby corrected as shown below:

Title page,
Item [73], Assignee, "Rosen Tantau Mathias; Tantau Nachfolger, both of (DE)" should read -- Rosen Tantau Mathias and Tantau Nachfolger, (DE) --.

Signed and Sealed this

Fourth Day of February, 2003

JAMES E. ROGAN
*Director of the United States Patent and Trademark Office*